United States Patent
Katakura

(10) Patent No.: US 9,851,551 B2
(45) Date of Patent: Dec. 26, 2017

(54) ENDOSCOPE WITH PLURALITY OF ILLUMINATION OPTICAL SYSTEMS

(71) Applicant: OLYMPUS CORPORATION, Hachioji-shi, Tokyo (JP)

(72) Inventor: Masahiro Katakura, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/341,257

(22) Filed: Nov. 2, 2016

(65) Prior Publication Data
US 2017/0052359 A1 Feb. 23, 2017

Related U.S. Application Data

(63) Continuation of application No. PCT/JP2015/077823, filed on Sep. 30, 2015.

(30) Foreign Application Priority Data

Oct. 6, 2014 (JP) .................................. 2014-205572

(51) Int. Cl.
*A61B 1/06* (2006.01)
*G02B 23/24* (2006.01)
(Continued)

(52) U.S. Cl.
CPC ...... *G02B 23/2438* (2013.01); *A61B 1/00096* (2013.01); *A61B 1/00188* (2013.01);
(Continued)

(58) Field of Classification Search
CPC ... A61B 1/00188; A61B 1/00163; A61B 1/06; A61B 1/07; A61B 1/00096;
(Continued)

(56) References Cited

U.S. PATENT DOCUMENTS 6,251,068 B1 * 6/2001 Akiba ................ A61B 1/00096
600/177
8,343,043 B2 1/2013 Kase et al.
(Continued)

FOREIGN PATENT DOCUMENTS

EP 2380483 A1 10/2011
JP 64026815 A 1/1989
(Continued)

OTHER PUBLICATIONS

International Search Report (ISR) and Written Opinion dated Feb. 16, 2016 issued in International Application No. PCT/JP2015/077823.

*Primary Examiner* — John P Leubecker
(74) *Attorney, Agent, or Firm* — Holtz, Holtz & Volek PC

(57) ABSTRACT

This endoscope has an observation optical system that switches its observation mode between magnified observation and normal observation by moving some lenses in an optical-axis direction; and a plurality of illumination optical systems, wherein lens surfaces at the most distal ends of the plurality of illumination optical systems are disposed closer to a proximal end than a lens surface at the most distal end of the observation optical system, and all of the lens surfaces at the most distal ends of the plurality of illumination optical systems are disposed substantially parallel to the lens surface at the most distal end of the observation optical system, wherein the following conditional expressions (1) to (3) are satisfied.

$$1.0 \leq D\_Back(far)/D\_Back(near) < 3.0 \quad (1)$$

$$0.015 < D\_Back(far)/D\_far < 1.0 \quad (2)$$

$$1.01 < \omega(wide)/\omega(tele) < 5.0 \quad (3)$$

4 Claims, 14 Drawing Sheets

(51) Int. Cl.
*A61B 1/00* (2006.01)
*A61B 1/07* (2006.01)
(52) U.S. Cl.
CPC .............. *A61B 1/06* (2013.01); *A61B 1/0676* (2013.01); *A61B 1/07* (2013.01); *G02B 23/2461* (2013.01); *G02B 23/2469* (2013.01)
(58) Field of Classification Search
CPC .............. G02B 23/2415; G02B 23/243; G02B 23/2438; G02B 6/005
USPC ........................................................ 600/177
See application file for complete search history.

(56) References Cited

U.S. PATENT DOCUMENTS

| | | | |
|---|---|---|---|
| 2006/0052668 A1* | 3/2006 | Homma | A61B 1/07 600/177 |
| 2009/0156898 A1* | 6/2009 | Ichimura | A61B 1/00089 600/127 |
| 2011/0077465 A1 | 3/2011 | Mizuyoshi et al. | |
| 2012/0245421 A1* | 9/2012 | Kitano | A61B 1/00039 600/180 |
| 2013/0109917 A1 | 5/2013 | Kase et al. | |
| 2013/0310649 A1* | 11/2013 | Sone | A61B 1/00096 600/177 |
| 2015/0257630 A1* | 9/2015 | Sone | A61B 1/00 600/109 |
| 2016/0256042 A1* | 9/2016 | Takato | G02B 23/26 |
| 2016/0295085 A1* | 10/2016 | Aoyama | H04N 5/2256 |
| 2016/0345811 A1* | 12/2016 | Sone | A61B 1/00 |

FOREIGN PATENT DOCUMENTS

| | | |
|---|---|---|
| JP | 10239740 A | 9/1998 |
| JP | 2000139820 A | 5/2000 |
| JP | 2011147757 A | 8/2011 |
| JP | 2012228443 A | 11/2012 |
| WO | 2011055640 A1 | 5/2011 |

* cited by examiner

ENDOSCOPE WITH PLURALITY OF ILLUMINATION OPTICAL SYSTEMS

CROSS-REFERENCE TO RELATED APPLICATIONS

This application is a Continuation application of International Application No. PCT/JP2015/077823 filed on Sep. 30, 2015, which claims priority to Japanese Application No. 2014-205572 filed on Oct. 6, 2014. The Contents of International Application No. PCT/JP2015/077823 and Japanese application No. 2014-205572 are hereby incorporated herein by reference in its entirety.

TECHNICAL FIELD

The present invention relates to an endoscope.

BACKGROUND ART

In the related art, there is a known endoscope in which a plurality of illumination optical systems are provided around an observation optical system in order to illuminate a field of view of the observation optical system with uniform brightness (for example, see PTL 1). The light-distribution irregularities of illumination light in the field of view become particularly problematic when performing magnified observation by bringing a distal-end surface of the endoscope close to an object at a distance that is equal to or less than 2 mm. In other words, because the distance between the distal-end surface of the endoscope and the object is very small, it is difficult to make the illumination light coming from the illumination optical systems reaches the entire field of view of the observation optical system. In the case of PTL 1, the layout of the illumination optical systems at the endoscope distal-end surface is designed so as to make improvement in the light-distribution irregularities during magnified observation.

CITATION LIST

Patent Literature

{PTL 1} Japanese Unexamined Patent Application, Publication No. 2000-139820

SUMMARY OF INVENTION

In order to achieve the above-described object, the present invention provides the following solutions.

The present invention provides an endoscope including: an observation optical system that switches between magnified observation and normal observation by moving a lens in an optical-axis direction; and a plurality of illumination optical systems that irradiate an object with illumination light beams, wherein at least one of the lens surfaces at the most distal ends of the plurality of illumination optical systems is disposed closer to a proximal end than a lens surface at the most distal end of the observation optical system, and all of the lens surfaces at the most distal ends of the plurality of illumination optical systems are disposed substantially parallel to the lens surface at the most distal end of the observation optical system, and also the following conditional expressions (1) to (3) are satisfied.

$$1.0 \leq D\_Back(far)/D\_Back(near) < 3.0 \quad (1)$$

$$0.015 < D\_Back(far)/D\_far < 1.0 \quad (2)$$

$$1.01 < \omega(wide)/\omega(tele) < 5.0 \quad (3)$$

Here, D_Back(far) is a distance in the optical-axis direction between the lens surface at the most distal end of the observation optical system and the lens surface at the most distal end of one of the illumination optical systems which is farthest in a radial direction from the observation optical system; D_Back(near) is a distance in the optical-axis direction between the lens surface at the most distal end of the observation optical system and the lens surface at the most distal end of another one of the illumination optical systems which is nearest in the radial direction from the observation optical system; D_far is a distance in the radial direction between the center of the lens surface at the most distal end of the observation optical system and that of the lens surface at the most distal end of the illumination optical system that is the farthest from the observation optical system in the radial direction; $\omega$(wide) is a half field angle of the observation optical system in the normal observation state; and $\omega$(tele) is a half field angle of the observation optical system in the magnified observation state.

In the above-described invention, Conditional Expressions (4) and (5) below are further satisfied.

$$0.01 < D\_Back(far)/F\_tele < 1.0 \quad (4)$$

$$0.01 < D\_Back(near)/D\_near < 0.7 \quad (5)$$

In the expressions, F_tele is a focal length of the observation optical system in the magnified observation state; and D_near is a distance in the radial direction between the center of the lens surface at the most distal end of the observation optical system and that of the lens surface at the most distal end of the illumination optical system that is the nearest from the observation optical system in the radial direction.

DESCRIPTION OF EMBODIMENT

An endoscope 1 according to an embodiment of the present invention will be described below with reference to FIGS. 1 and 2.

Figure 1:
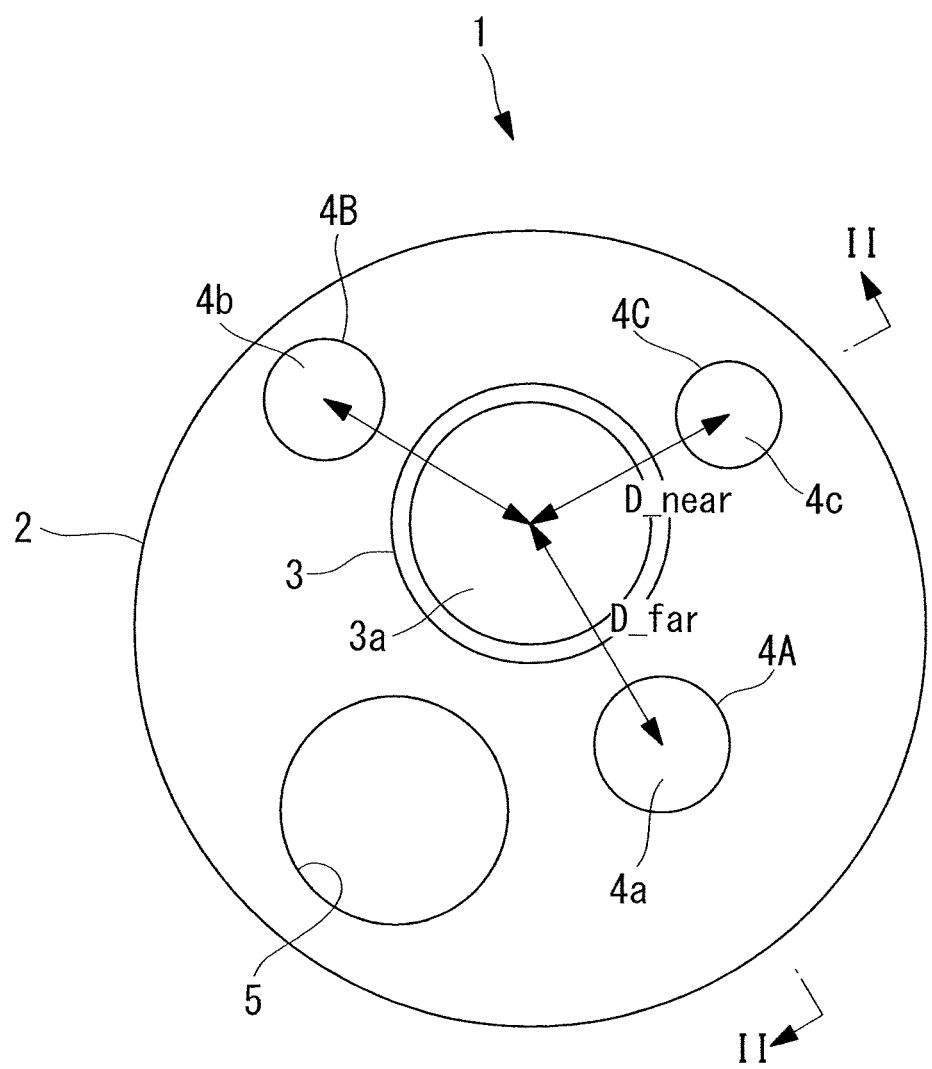
FIG. 1 is a front view of an endoscope according to an embodiment of the present invention.
Figure 2:
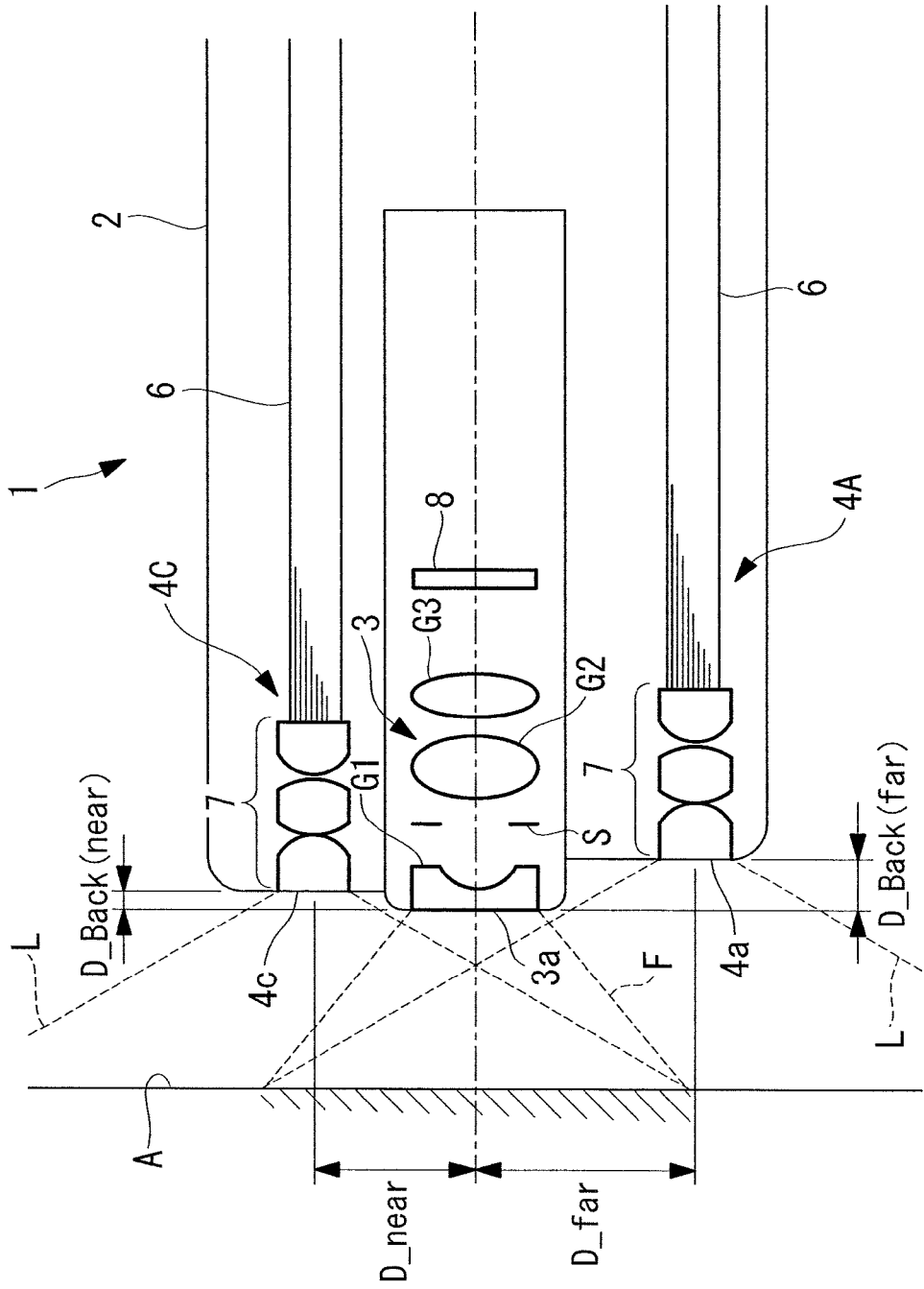
FIG. 2 is a cross-sectional view of a distal-end portion of the endoscope in FIG. 1 taken along II-II.

As shown in FIGS. 1 and 2, the endoscope 1 according to this embodiment is provided with, at a distal-end portion of an inserted portion 2, a single observation optical system 3, and three illumination optical systems 4A, 4B, and 4C. In the figure, the reference sign 5 is a forceps channel.

The observation optical system 3 has a first group G1 having positive refractive power, an aperture stop S, a second group G2, and a third group G3 having positive refractive power. The second group G2 is movable in an optical-axis direction, and it is possible to switch between normal observation and magnified observation by changing the magnification of the observation optical system 3 by moving the second group G2 in the optical-axis direction. In the normal observation state, the second group G2 is disposed at a first position on the optical axis, and, in the magnified observation state, the second group G2 is disposed at a second position, which is closer to the image (proximal end) than the first position, on the optical axis. Note that, although the groups G1, G2, and G3, each of which has a single lens, are shown in FIG. 2 in order to simplify the drawing, each of the groups G1, G2, and G3 may be composed of a plurality of lenses. In addition, the observation optical system 3 may additionally include an optical element having no power, such as a filter or the like, in addition to the lenses. Reference sign 8 is an image-acquisition element that acquires an object image formed by the observation optical system 3.

The illumination optical systems 4A, 4B, and 4C are provided at three locations, with spaces therebetween in the circumferential direction, around the observation optical system 3. Each of the illumination optical systems 4A, 4B, and 4C is provided with an optical-fiber bundle 6 that guides illumination light beam L coming from a light source (not shown) and a lens group 7 that is disposed at an emitting end of the optical-fiber bundle 6, and is configured to emit the illumination light L in the form of a diverging light beam by means of the lens group 7. Note that the number of illumination optical systems is not limited to three, and it may be two, four, or more.

The observation optical system 3 and all of the illumination optical systems 4A, 4B, and 4C have optical axes that are substantially parallel to each other. In addition, a most-distal-end lens surface (hereinafter referred to as "first lens surface") 3a of the observation optical system 3 and all of the lens surfaces (hereinafter referred to as "first lens surfaces") 4a, 4b, and 4c at the most distal ends of the illumination optical systems 4A, 4B, and 4C are disposed substantially parallel to each other. By doing so, the direction in which the illumination light L is emitted from each of the illumination optical systems 4A, 4B, and 4C and the observing direction of the observation optical system 3 are made parallel to each other, and thus, portions of the individual illumination light beams L illuminate a field of view F of the observation optical system 3 from three directions. In other words, the light distribution in the field of view F is a result of combining the illumination light L coming from the three illumination optical systems 4A, 4B, and 4C.

The first lens surfaces 4a, 4b, and 4c of the respective illumination optical systems 4A, 4B, and 4C are disposed at dented positions that are retracted toward the proximal end in the optical-axis direction with respect to the first lens surface 3a of the observation optical system 3. In the following, the distances in the optical-axis direction between the first lens surface 3a and the first lens surfaces 4a, 4b, and 4c will be referred to as "depth amounts".

The endoscope 1 of this embodiment satisfies Conditional Expressions (1) to (7) shown below.

$$1.0 \leq D\_Back(far)/D\_Back(near) < 3.0 \quad (1)$$

$$0.015 < D\_Back(far)/D\_far < 1.0 \quad (2)$$

$$1.01 < \omega(wide)/\omega(tele) < 5.0 \quad (3)$$

$$0.01 < D\_Back(far)/F\_tele < 1.0 \quad (4)$$

$$0.01 < D\_Back(near)/D\_near < 0.7 \quad (5)$$

$$0.06 < D\_Back(far)/enp(tele) < 1.0 \quad (6)$$

$$0.06 < D\_Back(near)/enp(tele) < 0.9 \quad (7)$$

Here, D_Back(far) is the depth amount of the farthest illumination optical system 4A; D_Back(near) is the depth amount of the nearest illumination optical system 4C; D_far is the distance in the radial direction between the centers of the lens surfaces 3a and 4a at the most distal ends of the observation optical system 3 and the farthest illumination optical system 4A; ω(wide) is the half field angle of the observation optical system 3 in the normal observation state; ω(tele) is the half field angle of the observation optical system 3 in the magnified observation state; F_tele is the focal length of the observation optical system 3 in the magnified observation state; D_near is the distance in the radial direction between the centers of the lens surfaces 3a and 4c at the most distal ends of the observation optical system 3 and the nearest illumination optical system 4C; and enp(tele) is the distance in the optical-axis direction between the lens surface 3a at the most distal end of the observation optical system 3 and the entrance pupil of the observation optical system 3 in the magnified observation state.

In examples shown in FIGS. 1 and 2, assuming that the distances in the radial direction between the centers of the first lens surface 3a and the first lens surfaces 4a, 4b, and 4c are Da, Db, and Dc, respectively, Da, Db, and Dc satisfy the following relation.

$$Da > Db > Dc$$

In other words, D_far=Da, and D_near=Dc.

Furthermore, assuming that the amount of the illumination light beam L emitted from the farthest illumination optical system 4A is Ia, and that the amount of the illumination light beam L emitted from the nearest illumination optical system 4C is Ic, Ia and Ic satisfy the following relation.

$$Ia > Ic$$

By increasing the amount of the illumination light beams L for the illumination optical system farther away from the observation optical system 3 in this way, the illumination light beams L emitted from the farthest and nearest illumination optical systems 4A and 4C are made to illuminate the field of view F at substantially equivalent brightness levels, and thus, it is possible to effectively reduce light-distribution irregularities in the circumferential direction in the field of view F.

In a general magnified observation endoscope, the distance between the lens surface 3a at the most distal end of the observation optical system 3 and an object A is set to be about 2 mm to 3 mm at which it is possible to perform good observation during magnified observation. In this way, during magnified observation, because the distance between the lens surface 3a at the most distal end of the observation optical system 3 and the object A is very small, it is difficult to make the illumination light beams coming from the illumination optical systems reach, in particular, the center region of the field of view F, and thus, the center region of the field of view F tends to be particularly dark.

With the endoscope 1 according to this embodiment, because the first lens surfaces 4a, 4b, and 4c of the illumination optical systems 4 are disposed at positions that are disposed at the dent positions and distant from the object A relative to the first lens surface 3a of the observation optical system 3, as compared with the case in which the observation optical system 3 and the illumination optical systems are disposed at the same heights, it is possible to make the illumination light beams L coming from the individual illumination optical systems 4A, 4B, and 4C reach a larger area in the field of view F. By doing so, it is possible to provide, even during magnified observation, good illumination over the entire region of the field of view F, including the center region thereof, by reducing the light-distribution irregularities in the field of view F.

Furthermore, the illuminated areas in the field of view F illuminated by the illumination light beams L coming from the individual illumination optical systems 4A, 4B, and 4C and brightness levels thereof depend on the distances, in the radial direction, of the illumination optical systems 4A, 4B, and 4C from the observation optical system 3. In other words, if the depth amounts of all of the illumination optical systems 4A, 4B, and 4C are equal to each other, although the nearest illumination optical system 4C can provide good illumination in a large area that includes the center region of the field of view F, the farthest illumination optical system 4A cannot provide sufficient illumination in the field of view F. As a result, in the field of view F, a region closer to the nearest illumination optical system 4A becomes bright, whereas a region closer to the farthest illumination optical system 4C becomes dark, thus causing pronounced light-distribution irregularities.

In this embodiment, the depth amounts of the illumination optical systems 4A and 4C, that is, D_Back(far) and D_Back(near), are designed in accordance with the distances thereto from the observation optical system 3 so as to satisfy Conditional Expressions (1), (2), and (4) to (7)$_m$ By doing so, it is possible to provide good illumination in the field of view F by using both the farthest illumination optical system 4A and the nearest illumination optical system 4C, and, even during magnified observation, it is possible to more effectively reduce the light-distribution irregularities in the field of view F.

In this embodiment, Conditional Expressions (1) to (7) are satisfied, it is preferable that Conditional Expressions (1')-(7') shown below are satisfied.

$$1.1 \leq D\_Back(far)/D\_Back(near) < 2.0 \qquad (1')$$

$$0.015 < D\_Back(far)/D\_far < 0.5 \qquad (2')$$

$$1.01 < \omega(wide)/\omega(tele) < 3.0 \qquad (3')$$

$$0.02 < D\_Back(far)/F\_tele < 0.6 \qquad (4')$$

$$0.015 < D\_Back(near)/D\_near < 0.3 \qquad (5')$$

$$0.1 < D\_Back(far)/enp(tele) < 0.7 \qquad (6')$$

$$0.09 < D\_Back(near)/enp(tele) < 0.6 \qquad (7')$$

In this embodiment, it is more preferable that Conditional Expressions (1")-(7") shown below are satisfied.

$$1.3 \leq D\_Back(far)/D\_Back(near) < 1.5 \qquad (1'')$$

$$0.02 < D\_Back(far)/D\_far < 0.2 \qquad (2'')$$

$$1.01 < \omega(wide)/\omega(tele) < 2.5 \qquad (3'')$$

$$0.03 < D\_Back(far)/F\_tele < 0.4 \qquad (4'')$$

$$0.02 < D\_Back(near)/D\_near < 0.15 \qquad (5'')$$

$$0.2 < D\_Back(far)/enp(tele) < 0.5 \qquad (6'')$$

$$0.2 < D\_Back(near)/enp(tele) < 0.45 \qquad (7'')$$

EXAMPLES

Next, Examples 1 to 3 of the endoscope according to the aforementioned embodiment will be described below with reference to FIGS. 3 to 14.

In the lens data of the examples, r is the radius of curvature (mm), d is the surface distance (mm), nd is the refractive index regarding the line d, vd is the Abbe number regarding the line d, symbol S is assigned to the surface number corresponding to the aperture stop. Also, the units of D_Back(far), D_Back(near), F_tele, D_far, D_near, and enp(tele) are mm, and the units of ω(wide) and ω(tele) are degree.

In the aberration diagrams (FIGS. 5, 6, 9, 10, 13, and 14) for the examples, symbol SA represents the spherical aberration, symbol AS represents the astigmatism, symbol DT represents the distortion, and symbol CC represents the chromatic aberration of magnification.

Table 1 which shows the numerals in Conditional Expressions (1) to (7) of Examples 1 to 3 is attached after explanations for Examples 1 to 3.

Example 1

Figure 3:
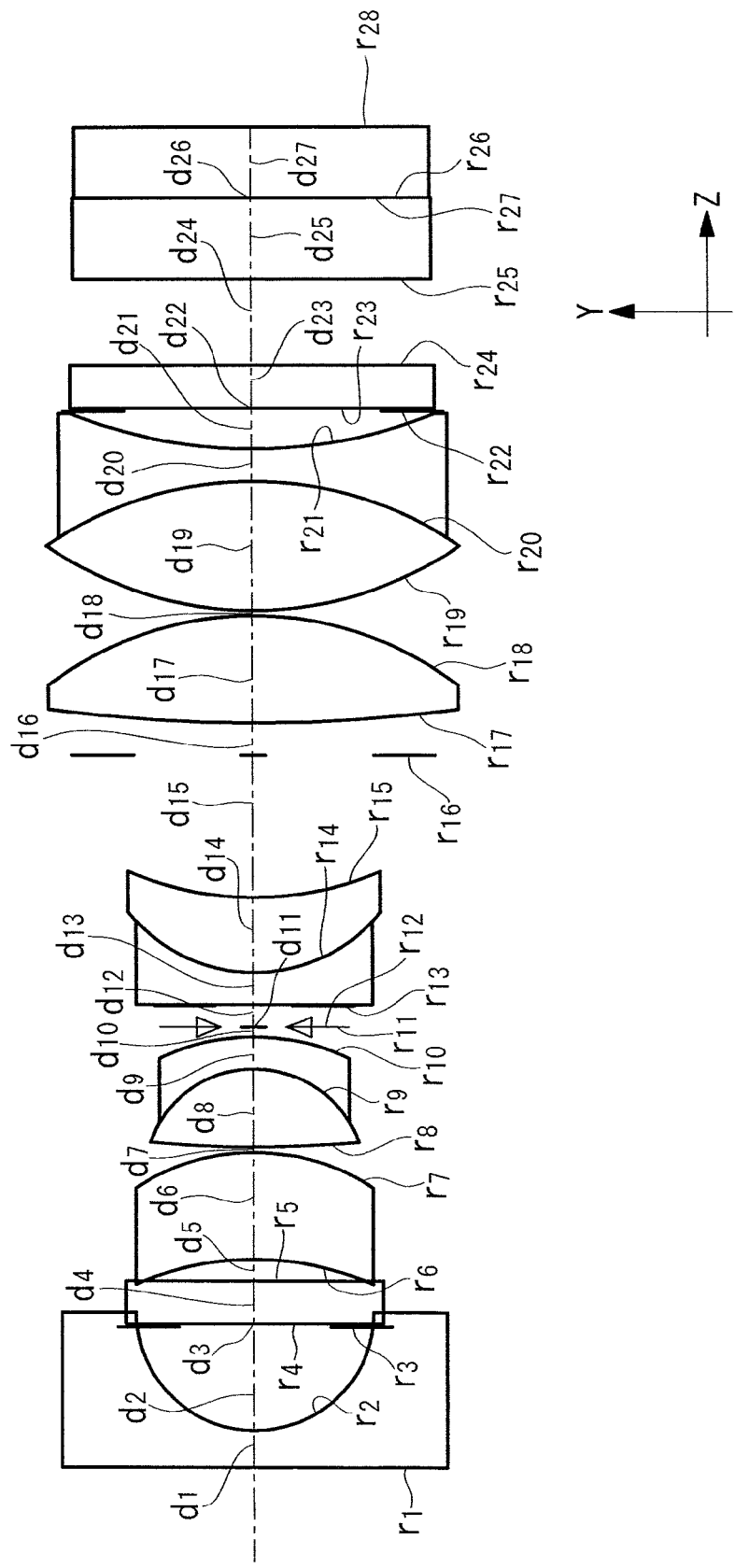
FIG. 3 is a longitudinal cross-sectional view showing a lens configuration of an observation optical system of an endoscope of Example 1, in which a normal observation state is shown.
Figure 4:
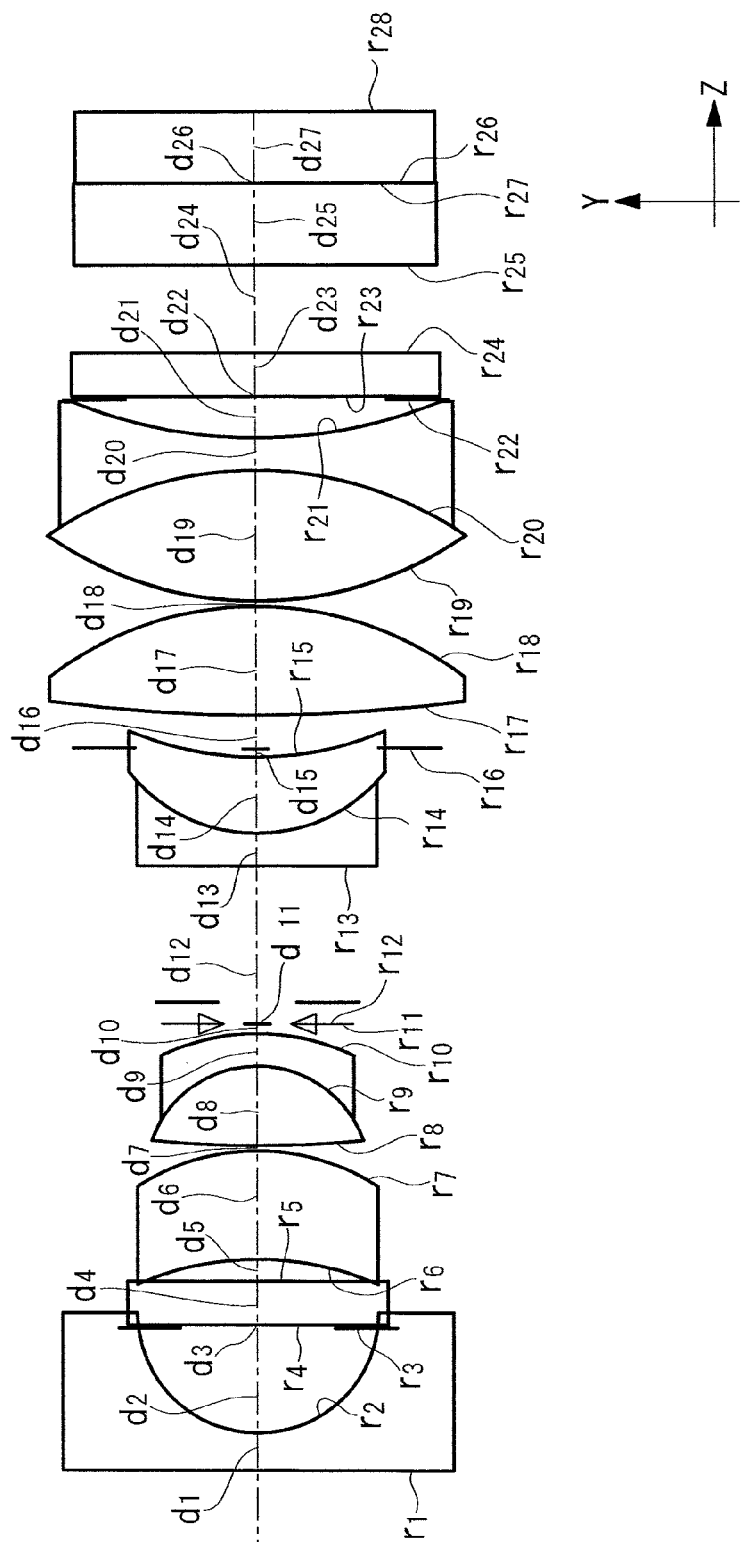
FIG. 4 shows a magnified observation state of the observation optical system in FIG. 3.
Figure 5:
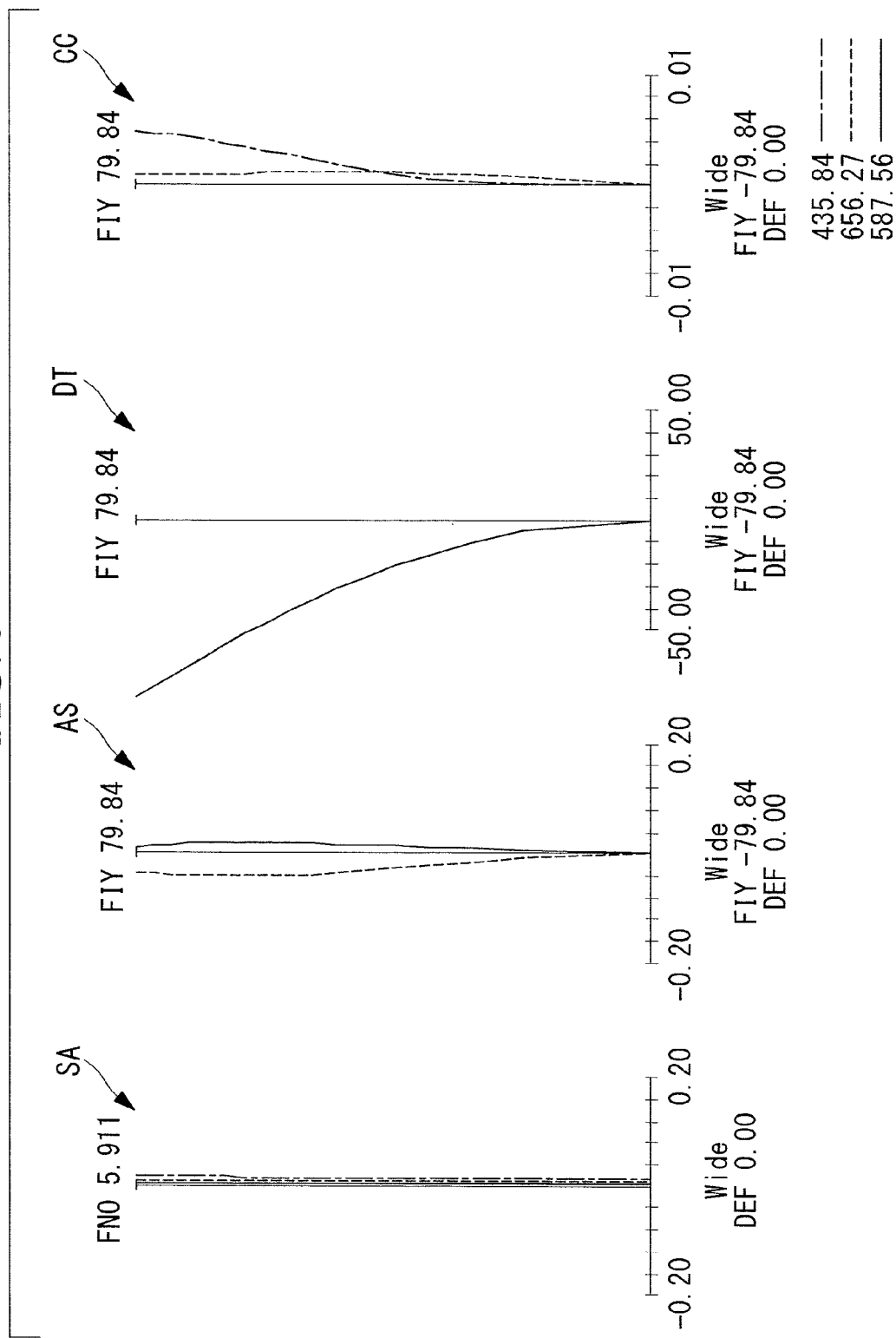
FIG. 5 is an aberration diagram showing spherical aberration (SA), astigmatism (AS), distortion (DT), and chromatic aberration of magnification (CC) of the observation optical system in FIG. 3 in the normal observation state.
Figure 6:
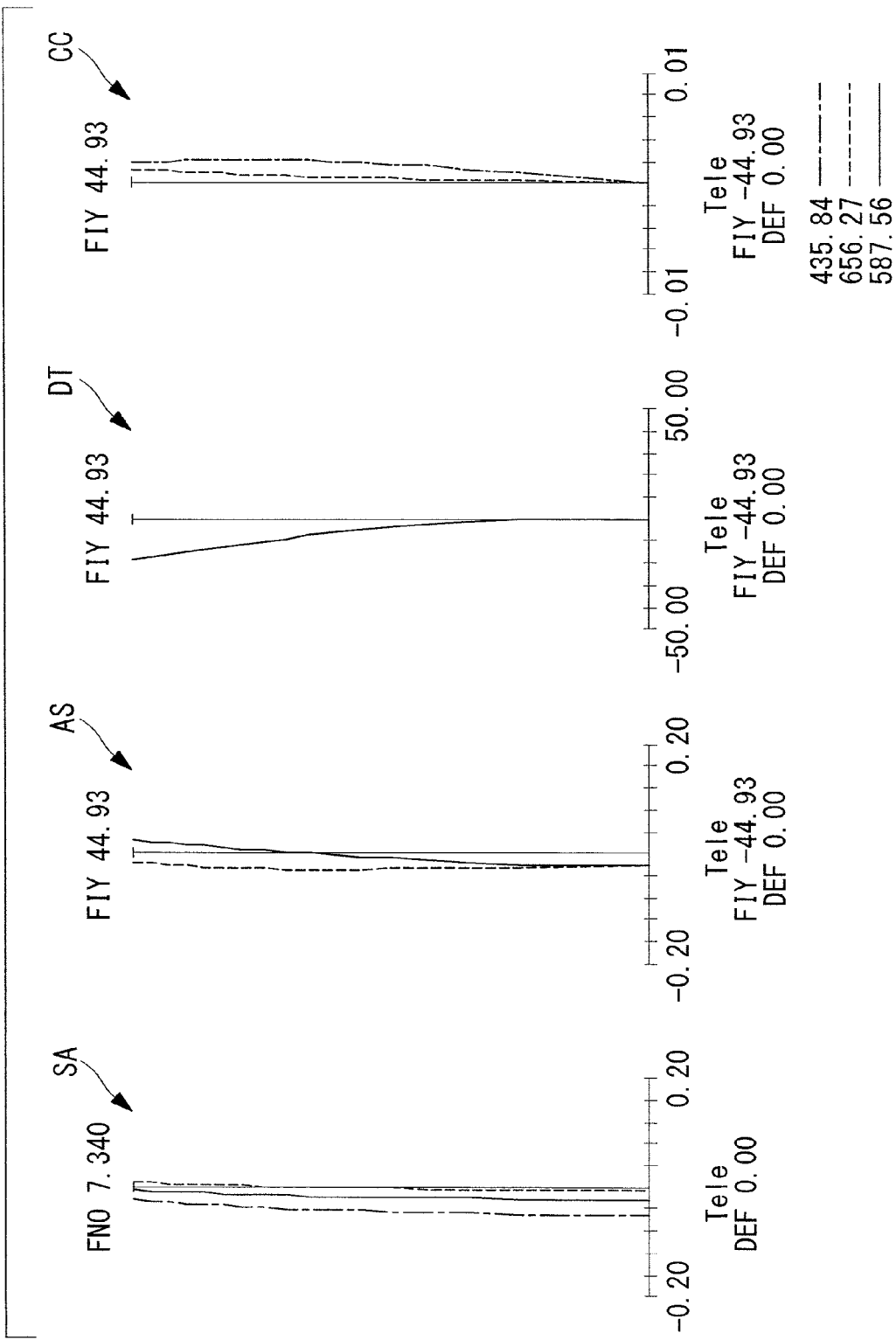
FIG. 6 is an aberration diagram showing spherical aberration (SA), astigmatism (AS), distortion (DT), and chromatic aberration of magnification (CC) of the observation optical system in FIG. 3 in the magnified observation state

The lens arrangement of the observation optical system of the endoscope according to Example 1 of the present invention is shown in FIGS. 3 and 4. FIG. 3 shows a normal observation state and FIG. 4 shows a magnified observation state, respectively. The aberration diagrams of the observation optical system in the normal observation state and the magnified observation state are shown in FIGS. 5 and 6.

In this example, the designed values of the endoscope are as follows. As shown in Table 1, the endoscope of this example satisfies Conditional Expressions (1) to (7) described above.

D_Back(far)=0.45
D_Back(near)=0.30
ω(wide)=79.922
ω(tele)=45.000
F_tele=1.2184
D_far=3.50
D_near=2.80
enp(tele)=0.9051

In this example, lens data and various data of the objective optical system is as follows.

| Lens data | | | | |
|---|---|---|---|---|
| Surface Number | r | d | nd | vd |
| 1 | ∞ | 0.30 | 1.88300 | 40.76 |
| 2 | 0.968 | 0.85 | | |
| 3 | ∞ | 0.03 | | |
| 4 | ∞ | 0.35 | 1.52100 | 65.12 |
| 5 | ∞ | 0.17 | | |
| 6 | −2.419 | 0.87 | 1.51633 | 64.14 |
| 7 | −1.767 | 0.04 | | |
| 8 | 8.931 | 0.64 | 1.69895 | 30.13 |
| 9 | −0.900 | 0.26 | 1.92286 | 18.90 |
| 10 | −1.779 | 0.08 | | |
| 11 (S) | ∞ | 0.17 | | |
| 12 | ∞ | d12 | | |
| 13 | ∞ | 0.26 | 1.77250 | 49.60 |
| 14 | 1.319 | 0.61 | 1.72825 | 28.46 |
| 15 | 2.608 | d15 | | |
| 16 | ∞ | 0.26 | | |
| 17 | 12.306 | 0.87 | 1.69680 | 55.53 |
| 18 | −2.753 | 0.04 | | |
| 19 | 2.969 | 1.04 | 1.80610 | 40.92 |
| 20 | −2.749 | 0.26 | 1.92286 | 18.90 |
| 21 | 3.963 | 0.30 | | |
| 22 | ∞ | 0.03 | | |
| 23 | ∞ | 0.35 | 1.52300 | 58.59 |
| 24 | ∞ | 0.70 | | |
| 25 | ∞ | 0.65 | 1.51633 | 64.14 |
| 26 | ∞ | 0.01 | 1.51300 | 64.01 |
| 27 | ∞ | 0.57 | 1.50510 | 63.26 |
| 28 (Image surface) | ∞ | | | |

| Various data | | |
|---|---|---|
| | Magnified observation | Normal observation |
| Focal length | 0.98 | 1.22 |
| FNO. | 5.91 | 7.34 |
| Field angle (2ω) | 159.84 | 90.00 |
| d12 | 0.01 | 1.09 |
| d15 | 1.16 | 0.07 |

| Focal length of each group | | |
|---|---|---|
| First group | Second group | Third group |
| 1.58 | −3.16 | 2.47 |

Example 2

Figure 7:
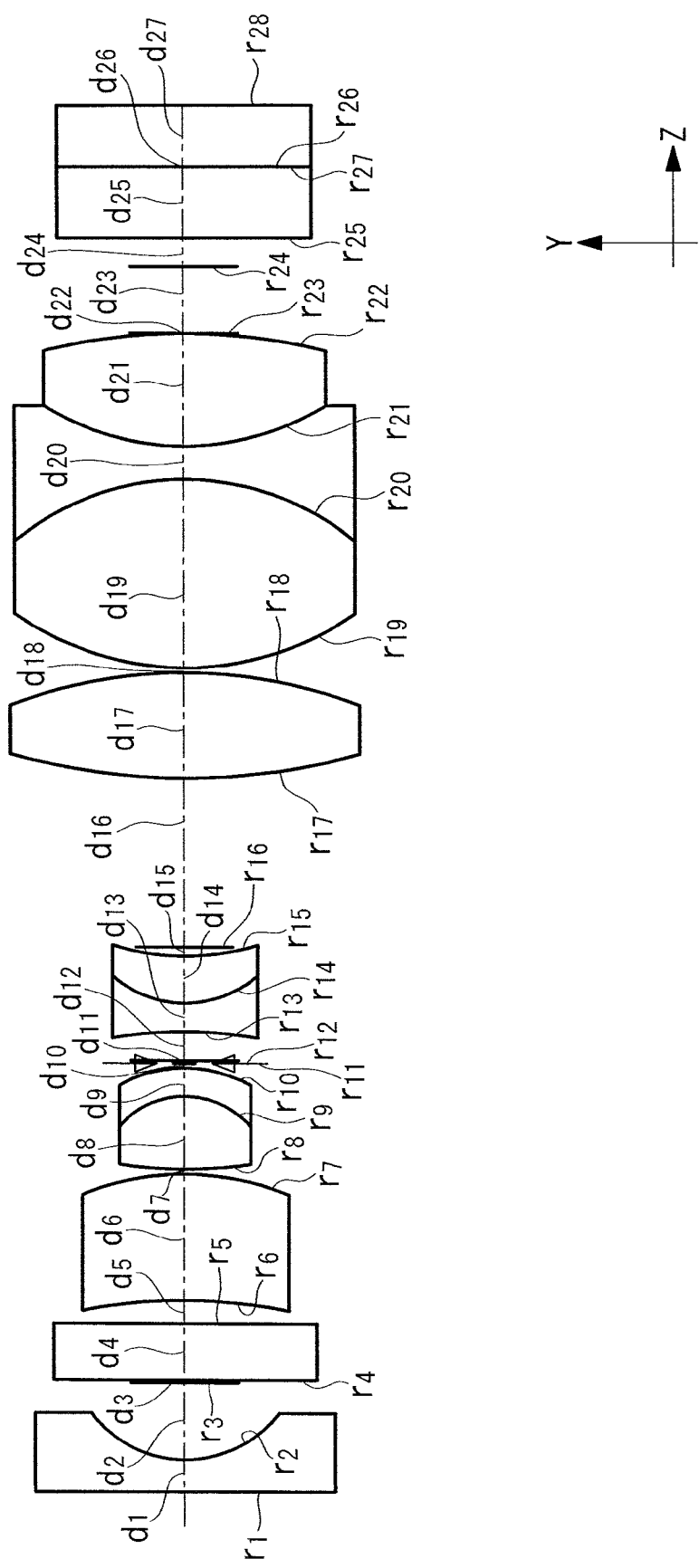
FIG. 7 is a longitudinal cross-sectional view showing a lens configuration of an observation optical system of an endoscope of Example 2, in which a normal observation state is shown.
Figure 8:
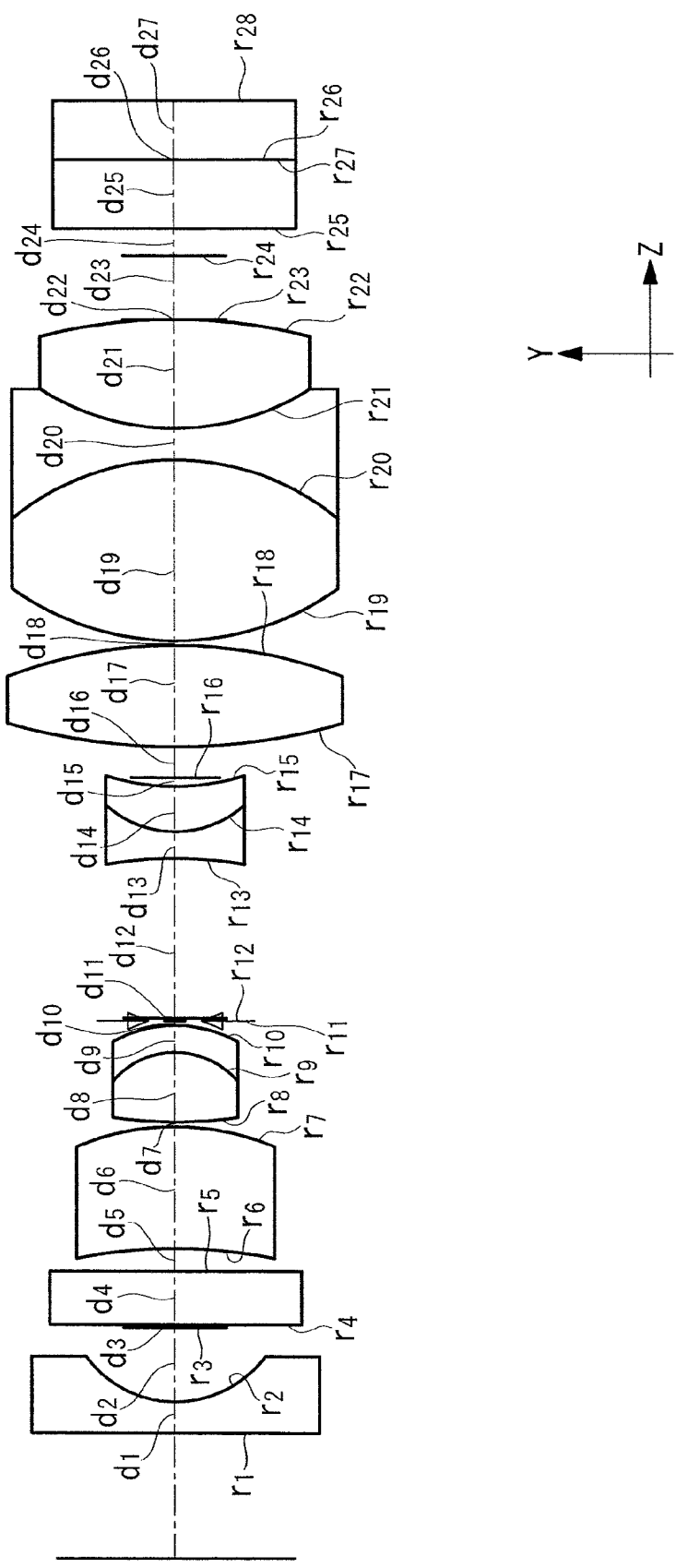
FIG. 8 shows a magnified observation state of the observation optical system in FIG. 7.
Figure 9:
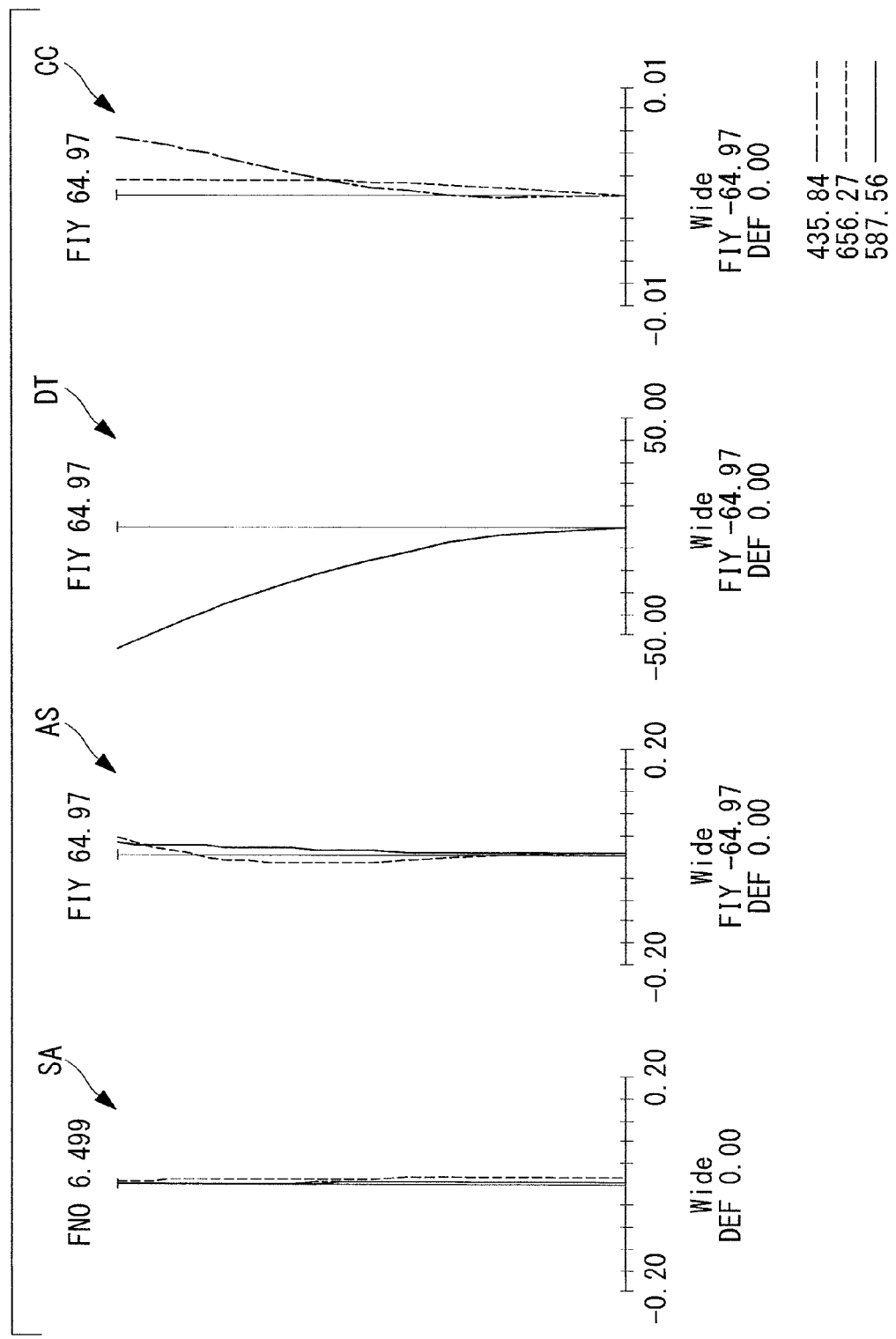
FIG. 9 is an aberration diagram showing spherical aberration (SA), astigmatism (AS), distortion (DT), and chromatic aberration of magnification (CC) of the observation optical system in FIG. 7 in the normal observation state.
Figure 10:
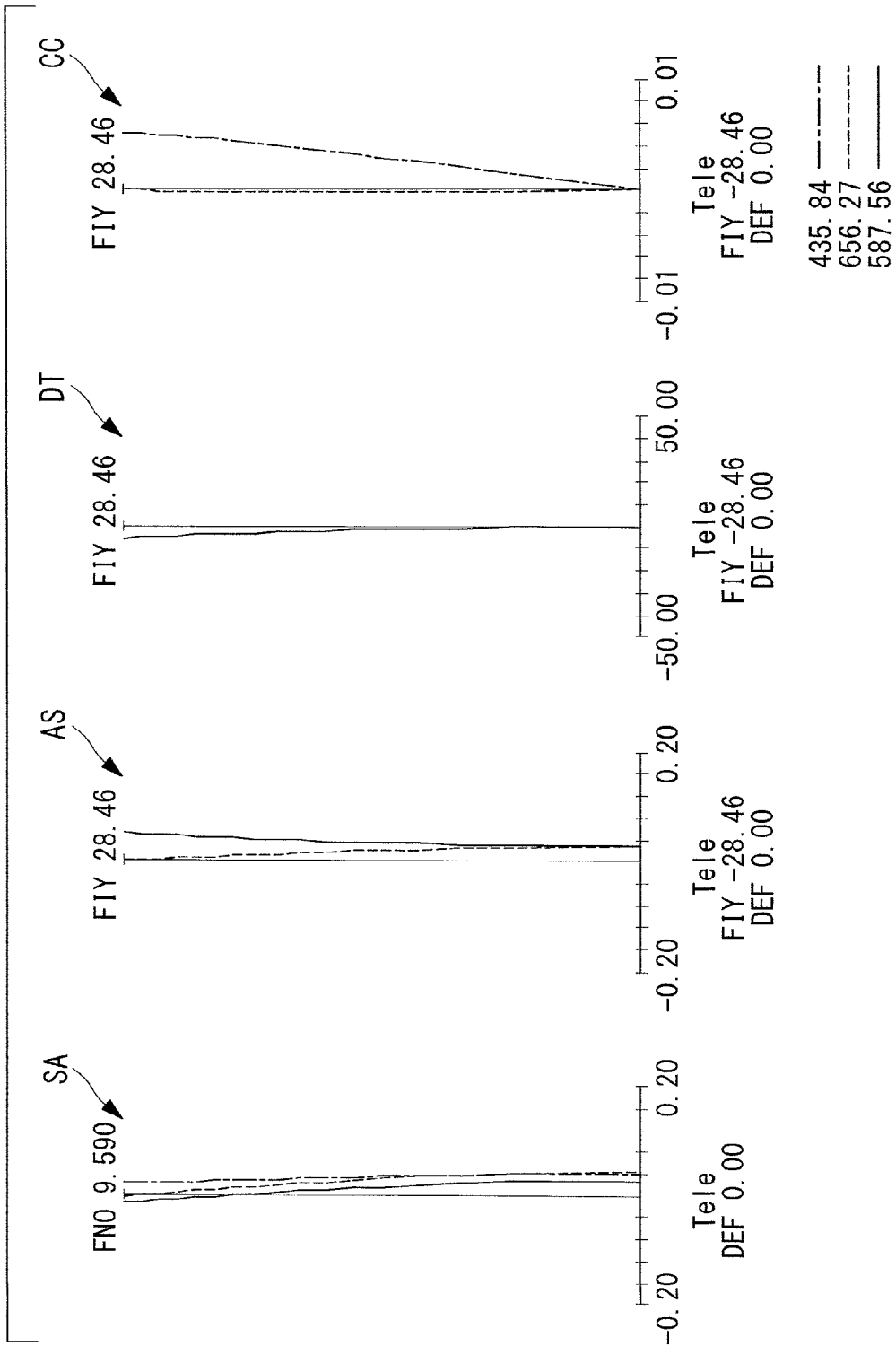
FIG. 10 is an aberration diagram showing spherical aberration (SA), astigmatism (AS), distortion (DT), and chromatic aberration of magnification (CC) of the observation optical system in FIG. 7 in the magnified observation state.

The lens arrangement of the observation optical system of the endoscope according to Example 2 of the present invention is shown in FIGS. 7 and 8. FIG. 7 shows a normal observation state and FIG. 8 shows a magnified observation state, respectively. The aberration diagrams of the observation optical system in the normal observation state and the magnified observation state are shown in FIGS. 9 and 10.

In this example, the designed values of the endoscope are as follows. As shown in Table 1, the endoscope of this example satisfies Conditional Expressions (1) to (7) described above.

D_Back(far)=0.48
D_Back(near)=0.40
ω(wide)=65.000
ω(tele)=28.500
F_tele=1.6263
D_far=2.80
D_near=2.70
enp(tele)=0.9928

In this example, lens data and various data of the objective optical system is as follows.

| Lens data | | | | |
|---|---|---|---|---|
| Surface Number | r | d | nd | vd |
| 1 | ∞ | 0.30 | 1.88300 | 40.76 |
| 2 | 1.078 | 0.72 | | |
| 3 | ∞ | 0.03 | | |
| 4 | ∞ | 0.52 | 1.52100 | 65.12 |
| 5 | ∞ | 0.22 | | |
| 6 | −4.855 | 1.17 | 1.58144 | 40.75 |
| 7 | −2.491 | 0.04 | | |
| 8 | 4.024 | 0.68 | 1.51742 | 52.43 |
| 9 | −0.800 | 0.26 | 1.92286 | 18.90 |
| 10 | −1.247 | 0.04 | | |
| 11 (S) | ∞ | 0.03 | | |
| 12 | ∞ | d12 | | |
| 13 | −3.861 | 0.26 | 1.77250 | 49.60 |
| 14 | 1.016 | 0.44 | 1.84666 | 23.78 |
| 15 | 2.209 | 0.09 | | |
| 16 | ∞ | d16 | | |
| 17 | 5.948 | 0.97 | 1.88300 | 40.76 |
| 18 | −4.540 | 0.04 | | |
| 19 | 2.726 | 1.74 | 1.51742 | 52.43 |
| 20 | −2.464 | 0.30 | 1.92286 | 18.90 |
| 21 | 2.437 | 1.04 | 1.58144 | 40.75 |
| 22 | −5.353 | 0.00 | | |
| 23 | ∞ | 0.61 | | |
| 24 | ∞ | 0.26 | | |
| 25 | ∞ | 0.65 | 1.51633 | 64.14 |
| 26 | ∞ | 0.01 | 1.51300 | 64.01 |
| 27 | ∞ | 0.57 | 1.50510 | 63.26 |
| 28 (Image surface) | ∞ | | | |

| Various data | | |
|---|---|---|
| | Magnified observation | Normal observation |
| Focal length | 1.10 | 1.63 |
| FNO. | 6.50 | 9.59 |
| Field angle (2ω) | 130.00 | 57.00 |
| d12 | 0.27 | 1.54 |
| d15 | 1.57 | 0.30 |

| Focal length of each group | | |
|---|---|---|
| First group | Second group | Third group |
| 1.25 | −1.88 | 2.45 |

Example 3

Figure 11:
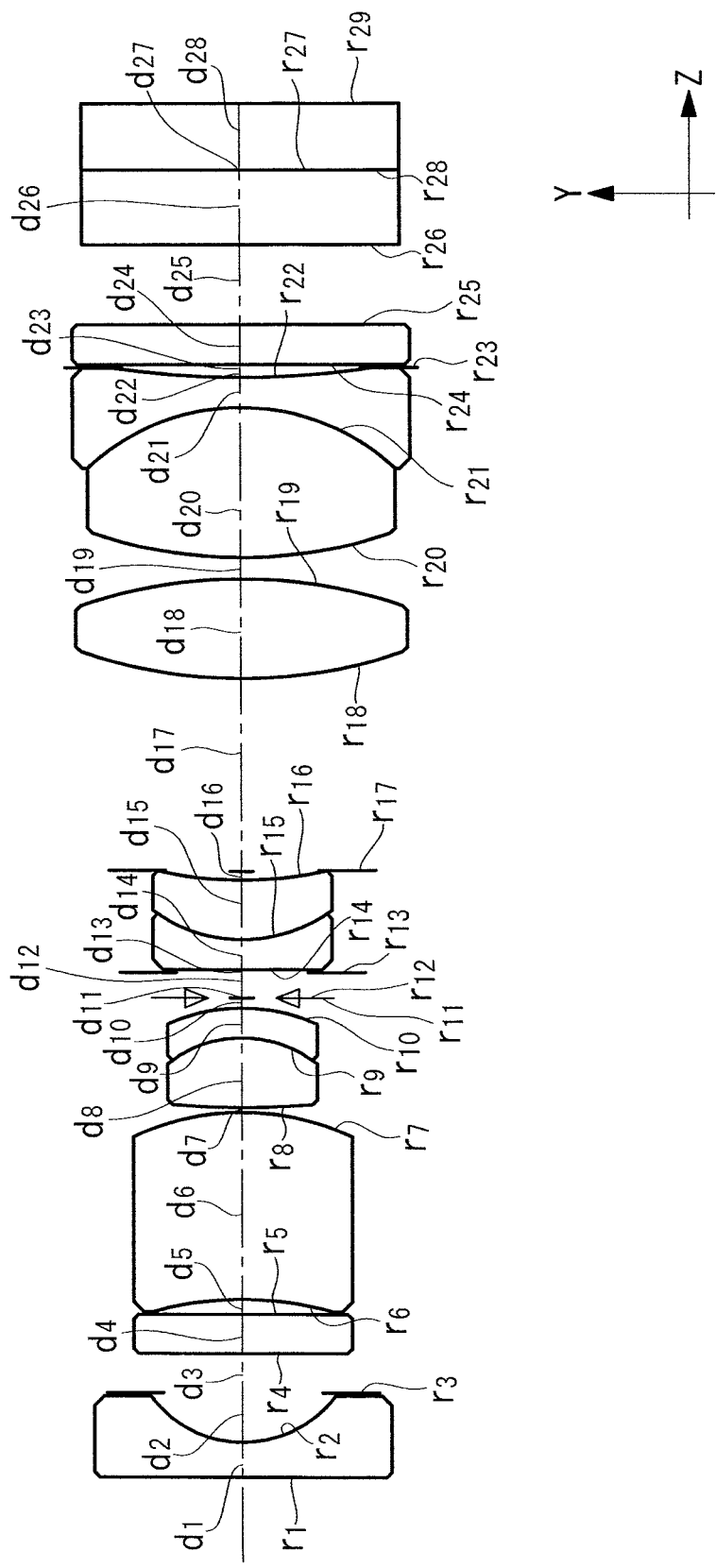
FIG. 11 is a longitudinal cross-sectional view showing a lens configuration of an observation optical system of an endoscope of Example 3, in which a normal observation state is shown.
Figure 12:
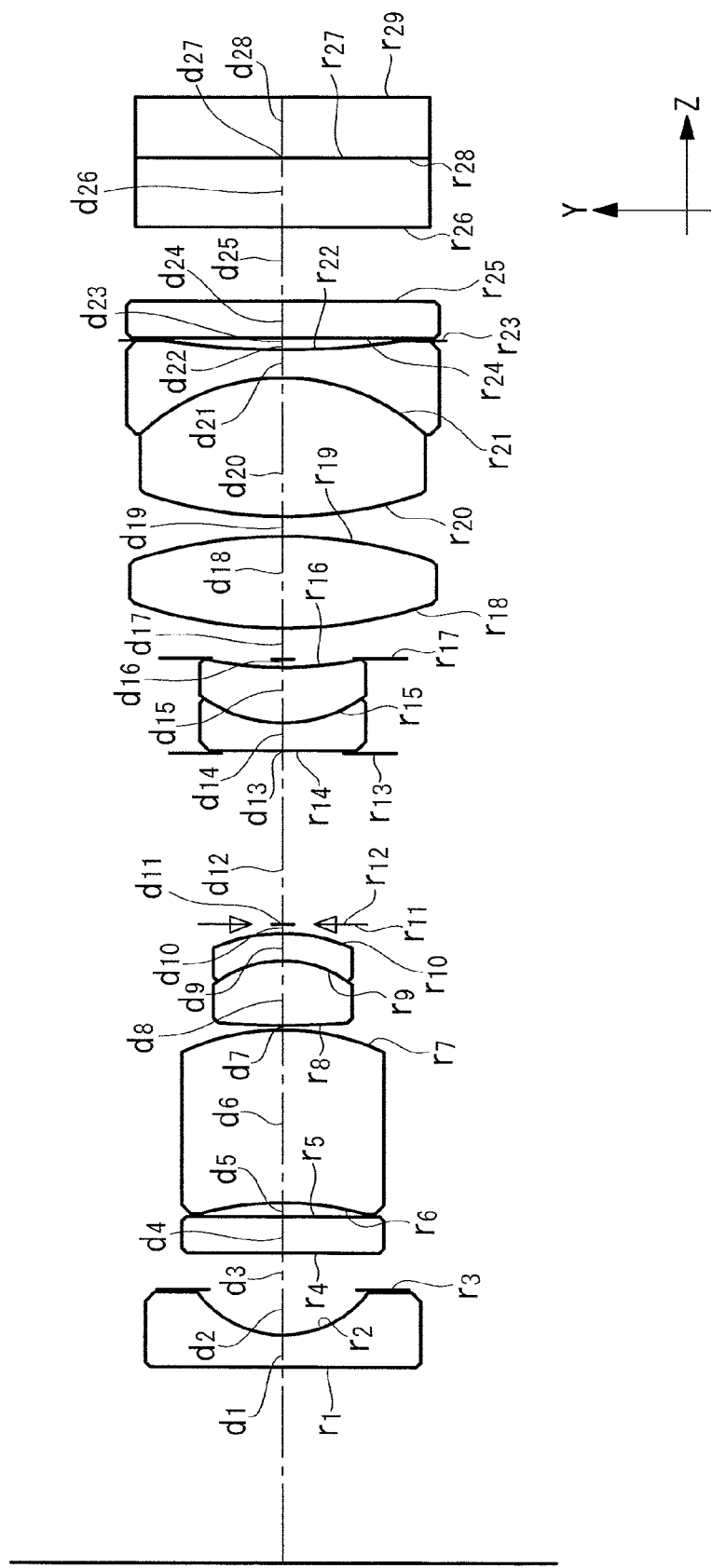
FIG. 12 shows a magnified observation state of the observation optical system in FIG. 11.
Figure 13:
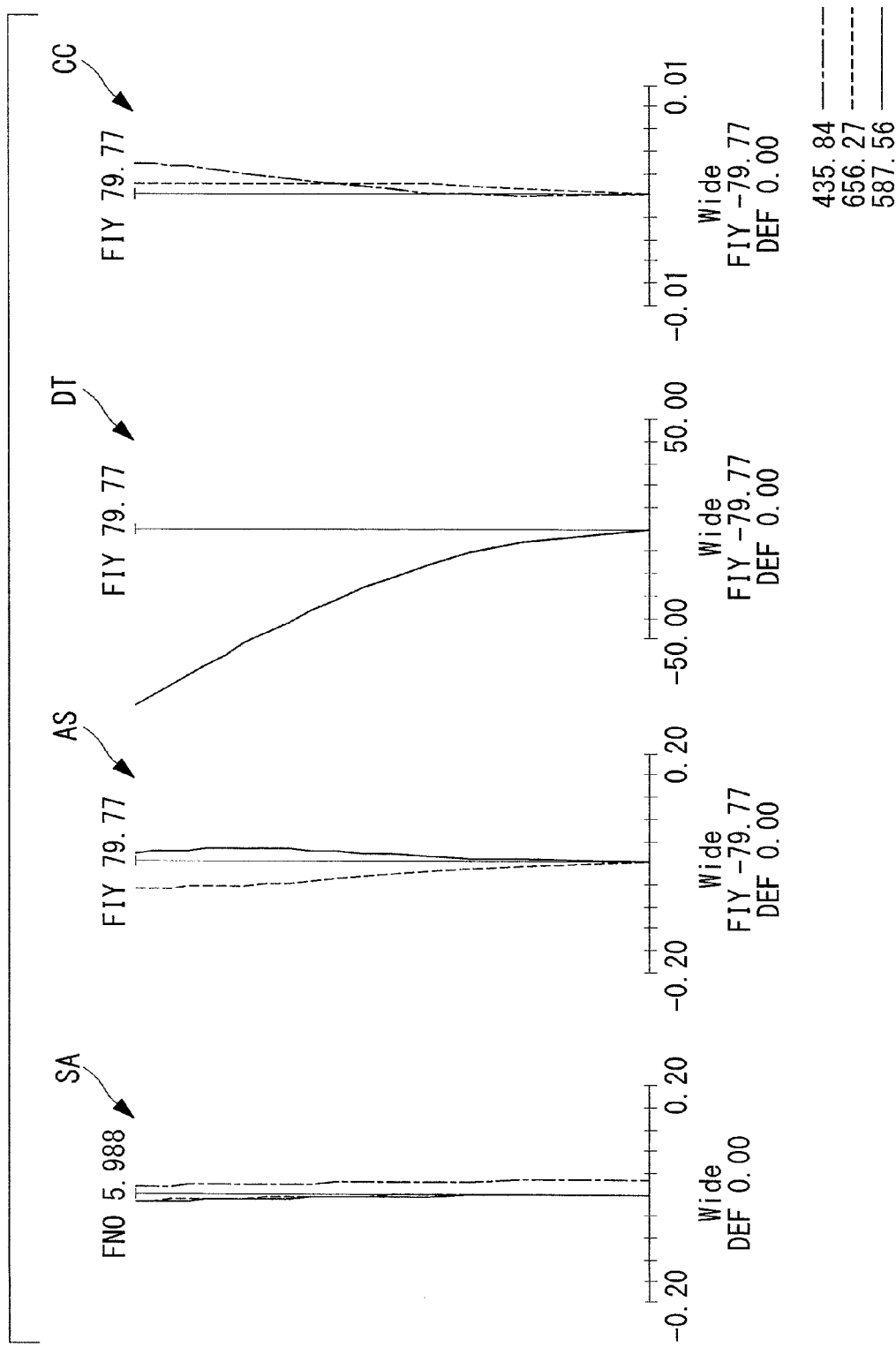
FIG. 13 is an aberration diagram showing spherical aberration (SA), astigmatism (AS), distortion (DT), and chromatic aberration of magnification (CC) of the observation optical system in FIG. 11 in the normal observation state.
Figure 14:
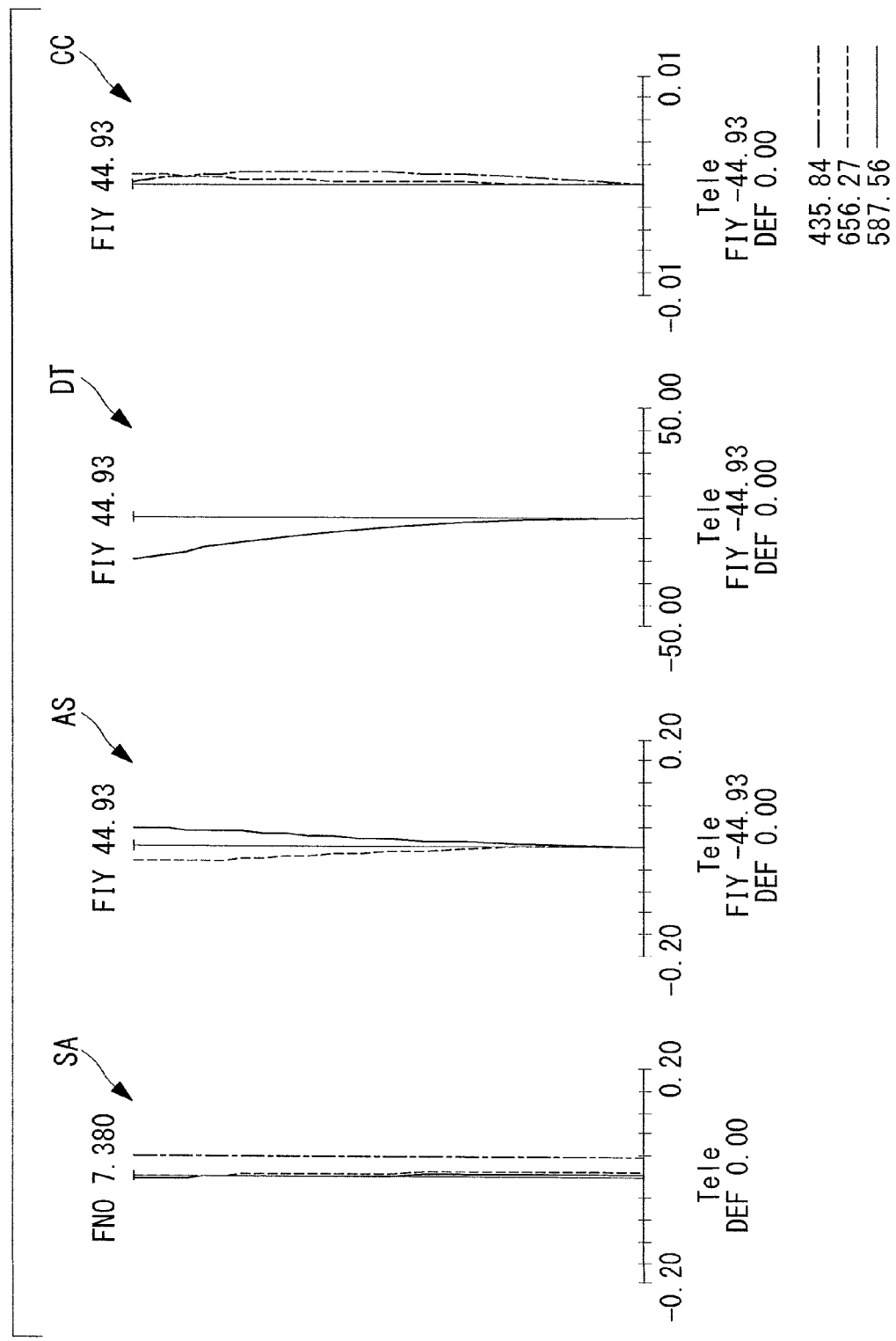
FIG. 14 is an aberration diagram showing spherical aberration (SA), astigmatism (AS), distortion (DT), and chromatic aberration of magnification (CC) of the observation optical system in FIG. 11 in the magnified observation state.

The lens arrangement of the observation optical system of the endoscope according to Example 3 of the present invention is shown in FIGS. 11 and 12. FIG. 11 shows a normal observation state and FIG. 12 shows a magnified observation state, respectively. The aberration diagrams of the observation optical system in the normal observation state and the magnified observation state are shown in FIGS. 13 and 14.

In this example, the designed values of the endoscope are as follows. As shown in Table 1, the endoscope of this example satisfies Conditional Expressions (1) to (7) described above.

D_Back(far)=0.25
D_Back(near)=0.25
ω(wide)=79.927
ω(tele)=45.001
F_tele=1.2124
D_far=3.00
D_near=2.50
enp(tele)=0.9400

In this example, lens data and various data of the objective optical system is as follows.

Lens data

| Surface Number | r | d | nd | vd |
| --- | --- | --- | --- | --- |
| 1 | ∞ | 0.30 | 1.88300 | 40.76 |
| 2 | 1.005 | 0.44 | | |
| 3 | ∞ | 0.35 | | |
| 4 | ∞ | 0.35 | 1.52100 | 65.12 |
| 5 | ∞ | 0.13 | | |
| 6 | −2.928 | 1.64 | 1.58144 | 40.75 |
| 7 | −2.269 | 0.04 | | |
| 8 | 7.900 | 0.61 | 1.51742 | 52.43 |
| 9 | −1.044 | 0.26 | 1.92286 | 18.90 |
| 10 | −1.600 | 0.09 | | |
| 11 (S) | ∞ | 0.00 | | |
| 12 | ∞ | d12 | | |
| 13 | ∞ | 0.03 | | |
| 14 | ∞ | 0.26 | 1.77250 | 49.60 |
| 15 | 1.305 | 0.52 | 1.72825 | 28.46 |
| 16 | 3.428 | 0.09 | | |
| 17 | ∞ | d17 | | |
| 18 | 4.379 | 0.87 | 1.81600 | 46.62 |
| 19 | −4.407 | 0.19 | | |
| 20 | 4.113 | 1.31 | 1.60300 | 65.44 |
| 21 | −1.984 | 0.26 | 1.92286 | 18.90 |
| 22 | 7.634 | 0.09 | | |
| 23 | ∞ | 0.03 | | |
| 24 | ∞ | 0.35 | 1.52300 | 58.59 |
| 25 | ∞ | 0.70 | | |
| 26 | ∞ | 0.65 | 1.51633 | 64.14 |
| 27 | ∞ | 0.01 | 1.51300 | 64.01 |
| 28 | ∞ | 0.57 | 1.50510 | 63.26 |
| 29 (Image | ∞ | | | |

Various data

| | Magnified observation | Normal observation |
| --- | --- | --- |
| Focal length | 0.98 | 1.21 |
| FNO. | 5.99 | 7.38 |
| Field angle (2ω) | 159.85 | 90.00 |
| d12 | 0.23 | 1.62 |
| d15 | 1.67 | 0.28 |

Focal length of each group

| First group | Second group | Third group |
| --- | --- | --- |
| 1.78 | −4.03 | 2.80 |

TABLE 1

| CONDITIONAL EXPRESSION | EXAMPLE 1 | EXAMPLE 2 | EXAMPLE 3 |
| --- | --- | --- | --- |
| (1) | 1.500 | 1.200 | 1.000 |
| (2) | 0.129 | 0.171 | 0.083 |
| (3) | 1.776 | 2.281 | 1.776 |
| (4) | 0.369 | 0.295 | 0.206 |
| (5) | 0.1071 | 0.1481 | 0.1000 |
| (6) | 0.497 | 0.483 | 0.266 |
| (7) | 0.331 | 0.403 | 0.266 |

The inventor has arrived at the following aspects of the invention.

An aspect of the present invention provides an endoscope including: an observation optical system that switches between magnified observation and normal observation by moving a lens in an optical-axis direction; and a plurality of illumination optical systems that irradiate an object with illumination light beams, wherein at least one of the lens surfaces at the most distal ends of the plurality of illumination optical systems is disposed closer to a proximal end than a lens surface at the most distal end of the observation optical system, and all of the lens surfaces at the most distal ends of the plurality of illumination optical systems are disposed substantially parallel to the lens surface at the most distal end of the observation optical system, and also the following conditional expressions (1) to (3) are satisfied.

$$1.0 \leq D\_Back(far)/D\_Back(near) < 3.0 \quad (1)$$

$$0.015 < D\_Back(far)/D\_far < 1.0 \quad (2)$$

$$1.01 < \omega(wide)/\omega(tele) < 5.0 \quad (3)$$

Here, D_Back(far) is a distance in the optical-axis direction between the lens surface at the most distal end of the observation optical system and the lens surface at the most distal end of one of the illumination optical systems which is farthest in a radial direction from the observation optical system; D_Back(near) is a distance in the optical-axis direction between the lens surface at the most distal end of the observation optical system and the lens surface at the most distal end of another one of the illumination optical systems which is nearest in the radial direction from the observation optical system; D_far is a distance in the radial direction between the center of the lens surface at the most distal end of the observation optical system and that of the lens surface at the most distal end of the illumination optical system that is the farthest from the observation optical system in the radial direction; ω(wide) is a half field angle of the observation optical system in the normal observation state; and ω(tele) is a half field angle of the observation optical system in the magnified observation state.

In a general magnified observation endoscope, the distance between the lens surface at the most distal end of the observation optical system and the object is set to be about 2 to 3 mm at which it is possible to perform good observation during magnified observation.

With the present invention, because the lens surfaces at the most distal ends of the illumination optical systems are disposed at positions that are disposed at dent positions relative to the lens surface at the most distal end of the observation optical system, as compared with a case in the related art in which the observation optical system and the illumination optical systems are disposed at the same heights, it is possible to effectively suppress the occurrence of light-distribution irregularities in the field of view of the observation optical system, in particular, during magnified observation. Hereinafter, in the present specification, the distances in the optical-axis direction between the lens surface at the most distal end of the observation optical system and the lens surfaces at the most distal ends of the respective illumination optical systems will be referred to as the "depth amounts".

Conditional Expression (1) indicates that the depth amount of the illumination optical system that is the farthest from the observation optical system in the radial direction is equal to or greater than the depth amount of the illumination optical system that is the nearest therefrom. when the conditions are within the range of the Conditional Expression (1), it is possible to achieve, even during the magnified observation, a good light distribution in the field of view. Hereinafter, the illumination optical system that is the farthest from the observation optical system in the radial direction when measuring the distance from the optical axis of the observation optical system will be referred to as "farthest illumination optical system", and the illumination optical system that is the nearest therefrom will be referred to as "nearest illumination optical system".

When the conditions do not reach the lower limit of Conditional Expression (1), the depth amount of the nearest illumination optical system becomes larger than the depth amount of the farthest illumination optical system. In this case, in the field of view, the balance between the brightness of the illumination light beam coming from the nearest illumination optical system and that of the illumination light beam coming from the farthest illumination optical system is deteriorated, thus causing light-distribution irregularities.

When the conditions exceed the upper limit of Conditional Expression (1), because the farthest illumination optical system is disposed at a too deep position, the illumination light from the furthest illumination optical system may be blocked by the observation optical system or the like, and thus, it becomes impossible to achieve a good light distribution.

Conditional Expression (2) defines the ratio between the distance to the farthest illumination optical system from the observation optical system and the depth amount of the farthest illumination optical system. When the conditions exceed the upper limit of Conditional Expression (2), because the farthest illumination optical system is disposed at a too deep position, the illumination light from the furthest illumination optical system may be blocked by the observation optical system or the like, and thus, it becomes impossible to achieve a good light distribution. When the conditions do not reach the lower limit of Conditional Expression (2), because the distance between the farthest illumination optical system and the observation optical system is too large, it is difficult to make the illumination light beam coming from the farthest illumination optical system reach in an effective way the field of view during magnified observation, and thus, it becomes impossible to achieve a good light distribution.

Conditional Expression (3) defines the ratios of the half field angles of the observation optical system during the normal observation state and the magnified observation state. In the endoscope that satisfies Conditional Expression (3), pronounced effects of Conditional Expressions (1) and (2) are achieved. In other words, when the conditions are equal to or above the upper limit of Conditional Expression (3), the angle of observation view of the observation optical system in the magnified observation state becomes small, and, when the conditions are equal to or below the lower limit of Conditional Expression (3), the observation optical system acts essentially as a fixed-focus lens, and thus, in both cases, the light-distribution irregularities during magnified observation cause almost no problem.

In the above-described invention, it is preferable that Conditional Expressions (4) and (5) below be satisfied.

$$0.01 < D\_Back(far)/F\_tele < 1.0 \quad (4)$$

$$0.01 < D\_Back(near)/D\_near < 0.7 \quad (5)$$

In the expressions, F_tele is a focal length of the observation optical system in the magnified observation state; and D_near is a distance in the radial direction between the center of the lens surface at the most distal end of the observation optical system and that of the lens surface at the most distal end of the illumination optical system that is the nearest from the observation optical system in the radial direction.

Conditional Expression (4) defines the ratio between the focal length of the observation optical system in the magnified observation state and the depth amount of the farthest illumination optical system. Conditional Expression (5) defines the distance between the nearest illumination optical system and the observation optical system and the depth amount of the nearest illumination optical system. By satisfying Conditional Expressions (4) and (5), it is possible to further reduce the light-distribution irregularities of the illumination light in the field of view, and thus, it is possible to illuminate the field of view with more uniform brightness.

When the conditions exceed the upper limit of Conditional Expression (4), the angle of observation view is increased because the focal length of the observation optical system becomes too large, and thus, the arrangement design of the illumination optical systems of the present invention has little effect. When the conditions do not reach the lower limit of Conditional Expression (4), because the depth amount of the farthest illumination optical system is too small, it becomes difficult to make the illumination light beam coming from the farthest illumination optical system reach in an effective way the field of view during magnified observation, and thus, it becomes impossible to achieve a good light distribution.

When the condition exceed the upper limit of Conditional Expression (5), because the depth amount of the farthest illumination optical system is too large, the illumination light may be blocked by the observation optical system or the like, and thus, it becomes impossible to achieve a good light distribution. When the conditions do not reach the lower limit of Conditional Expression (5), because the depth amount of the farthest illumination optical system is too small, it becomes difficult to make the illumination light beam coming from the farthest illumination optical system reach in an effective way the field of view during magnified observation, and thus, it becomes impossible to achieve a good light distribution.

In the above-described invention, it is preferable that Conditional Expressions (6) and (7) below be satisfied.

$$0.06 < D\_Back(far)/enp(tele) < 1.0 \quad (6)$$

$$0.06 < D\_Back(near)/enp(tele) < 0.9 \quad (7)$$

In the expressions, enp(tele) is a distance in the optical-axis direction between the lens surface at the most distal end of the observation optical system and the entrance pupil of the observation optical system in the magnified observation state.

Conditional Expressions (6) and (7) define the relationship between the depth amount of the farthest or the nearest illumination optical system and the entrance-pupil position of the observation optical system. Within the range in which Conditional Expressions (6) and (7) are satisfied, because appropriate relationships are achieved between the depth amounts of the respective illumination optical systems and the entrance-pupil position, which makes the positional relationship between the field of view of the observation optical system and the area illuminated by the illumination optical systems appropriate, and thus, it is possible to further reduce the light-distribution irregularities.

When the conditions exceed the upper limits of Conditional Expressions (6) and (7), because the depth amounts of the illumination optical systems are too large, the illumination light may be blocked by the observation optical system or the like, and thus, it becomes impossible to achieve a good light distribution. When the conditions do not reach the lower limits of Conditional Expressions (6) and (7), because the entrance-pupil position is positioned too far on the image side, it is necessary to increase the diameter of the lens at the distal end in order to ensure an angle of observation view. As a result, the distances to the illumination optical systems from the observation optical system are increased, and thus, it becomes impossible to achieve a good light distribution.

In the above-described invention, it is preferable that an amount of light emitted from the illumination optical system that is the farthest from the observation optical system in the radial direction is greater than an amount of light emitted from each of the rest of the illumination optical systems.

By increasing the amount of light emitted from the illumination optical systems depending on the distances from the observation optical system in this way, a good balance is achieved, in the field of view, among the brightness levels of the illumination light coming from the respective illumination optical systems, and thus, it is possible to further reduce the light-distribution irregularities.

In the above-described invention, it is preferable that the three illumination optical systems are arranged in a circumferential direction with spaces therebetween and around the observation optical system.

By doing so, it is possible to further reduce the light-distribution irregularities in the field of view during magnified observation. In the case in which two illumination optical systems are provided, the light-distribution irregularities in the field of view become pronounced, and thus, it is difficult to satisfactorily reduce the light-distribution irregularities. In the case in which four or more illumination optical systems are provided, although a good light distribution is achieved, this configuration is not desirable because the outer diameter of the endoscope is increased.

Advantageous Effects of Invention

The aforementioned aspects afford an advantage in which it is also possible to effectively reduce light-distribution irregularities of illumination light in a field of view during magnified observation.

REFERENCE SIGNS LIST 1 endoscope
3 observation optical system
3a, 4a, 4b, 4c first lens surface (most-distal-end lens surface)
4A, 4B, 4C illumination optical system.

The invention claimed is:
1. An endoscope comprising:
an observation optical system that switches its observation mode between magnified observation and normal observation by moving a lens in an optical-axis direction; and
a plurality of illumination optical systems that irradiate an object with illumination light,
wherein lens surfaces at the most distal ends of the plurality of illumination optical systems are disposed closer to a proximal end than a lens surface at the most distal end of the observation optical system, and all of the lens surfaces at the most distal ends of the plurality of illumination optical systems are disposed substantially parallel to the lens surface at the most distal end of the observation optical system, and
wherein the following conditional expressions (1) to (5) are satisfied:

$$1.0 \leq D\_Back(far)/D\_Back(near) < 3.0 \quad (1)$$

$$0.015 < D\_Back(far)/D\_far < 1.0 \quad (2)$$

$$1.01 < \omega(wide)/\omega(tele) < 5.0 \quad (3)$$

$$0.01 < D\_Back(far)/F\_tele < 1.0 \quad (4)$$

$$0.01 < D\_Back(near)/D\_near < 0.7 \quad (5),$$

wherein:
D_Back(far) is a distance in the optical-axis direction between the lens surface at the most distal end of the observation optical system and the lens surface at the most distal end of one of the illumination optical systems which is farthest in a radial direction from the observation optical system;
D_Back(near) is a distance in the optical-axis direction between the lens surface at the most distal end of the observation optical system and the lens surface at the most distal end of another one of the illumination optical systems which is nearest in the radial direction to the observation optical system;
D_far is a distance in the radial direction between a center of the lens surface at the most distal end of the observation optical system and that of the lens surface at the most distal end of the illumination optical system that is the farthest from the observation optical system in the radial direction;
$\omega$(wide) is a half field angle of the observation optical system in the normal observation state;
$\omega$(tele) is a half field angle of the observation optical system in the magnified observation state;
F_tele is a focal length of the observation optical system in the magnified observation state; and
D_near is a distance in the radial direction between the center of the lens surface at the most distal end of the observation optical system and that of the lens surface at the most distal end of the illumination optical system that is the nearest to the observation optical system in the radial direction.
2. The endoscope according to claim 1, wherein the following conditional expressions (6) and (7) are satisfied:

$$0.06 < D\_Back(far)/enp(tele) < 1.0 \quad (6)$$

$$0.06 < D\_Back(near)/enp(tele) < 0.9 \quad (7),$$

wherein enp(tele) is a distance in the optical-axis direction between the lens surface at the most distal end of the observation optical system and an entrance pupil of the observation optical system in the magnified observation state.

3. The endoscope according to claim 1, wherein an amount of light emitted from the illumination optical system that is the farthest from the observation optical system in the radial direction is greater than an amount of light emitted from each of the rest of the illumination optical systems.

4. The endoscope according to claim 1, wherein the plurality of illumination optical systems comprise three illumination optical systems, and the three illumination optical systems are arranged in a circumferential direction with spaces therebetween and around the observation optical system.

* * * * *